United States Patent
Plumptre

(10) Patent No.: US 8,568,364 B2
(45) Date of Patent: Oct. 29, 2013

(54) DRUG DELIVERY DEVICE

(75) Inventor: David Plumptre, Droitwich Spa Worcestershire (GB)

(73) Assignee: Sanofi-Aventis Deutschland GmbH, Frankfurt am Main (DE)

(*) Notice: Subject to any disclaimer, the term of this patent is extended or adjusted under 35 U.S.C. 154(b) by 0 days.

(21) Appl. No.: 13/139,919

(22) PCT Filed: Dec. 18, 2009

(86) PCT No.: PCT/EP2009/067477
§ 371 (c)(1),
(2), (4) Date: Oct. 11, 2011

(87) PCT Pub. No.: WO2010/072661
PCT Pub. Date: Jul. 1, 2010

(65) Prior Publication Data
US 2012/0022462 A1    Jan. 26, 2012

(30) Foreign Application Priority Data
Dec. 23, 2008  (EP) .................. 08022318

(51) Int. Cl.
*A61M 5/32* (2006.01)
*A61M 3/00* (2006.01)
*A61M 5/00* (2006.01)

(52) U.S. Cl.
USPC ............ 604/197; 604/189; 604/232; 604/263

(58) Field of Classification Search
USPC .......... 604/197, 189, 232, 263; 220/780, 788; 215/318, 321; 206/363, 364, 367, 438, 206/305
See application file for complete search history.

(56) References Cited

U.S. PATENT DOCUMENTS

| 5,259,840 | A | 11/1993 | Boris |
| 5,735,827 | A | 4/1998 | Adwers et al. |
| 6,210,369 | B1 * | 4/2001 | Wilmot et al. ............... 604/157 |
| 6,454,746 | B1 * | 9/2002 | Bydlon et al. ............... 604/227 |

(Continued)

FOREIGN PATENT DOCUMENTS

| EP | 0327910 | 8/1989 |
| EP | 1007115 | 6/2000 |
| EP | 1923083 | 5/2008 |

OTHER PUBLICATIONS

International Preliminary Report on Patentability for International Application No. PCT/EP2009/067477, dated Jul. 7, 2011.
European Search Report for EP App. No. 08082311.8, dated May 11, 2009.

(Continued)

*Primary Examiner* — Bhisma Mehta
*Assistant Examiner* — Lauren M Peng
(74) *Attorney, Agent, or Firm* — McDonnell Boehnen Hulbert & Berghoff LLP

(57) ABSTRACT

A drug delivery device (1) comprises a housing (2) and a cap (3) attachable onto the housing (2). The cap (3) comprises one or more snap features (33) to attach the cap (3) onto the housing (2) and one or more orientation features (34) to define the orientation of the cap (3) relative to the housing (2). At least one of the orientation features (34) is located at a rigid part of the cap (3) and at least one of the snap features (34) is located at a less rigid part of the cap (3).

15 Claims, 3 Drawing Sheets

(56) References Cited

U.S. PATENT DOCUMENTS

2005/0113764 A1\* 5/2005 Watkins ........................ 604/197
2006/0206057 A1 9/2006 DeRuntz et al.
2008/0108951 A1\* 5/2008 Jerde et al. ................... 604/198

OTHER PUBLICATIONS

International Search Report for International App. No. PCT/EP2009/067477, mailed Apr. 28, 2010.
International Preliminary Report on Patentability for International App. No. PCT/EP2009/067477, dated Jun. 29, 2011.

\* cited by examiner

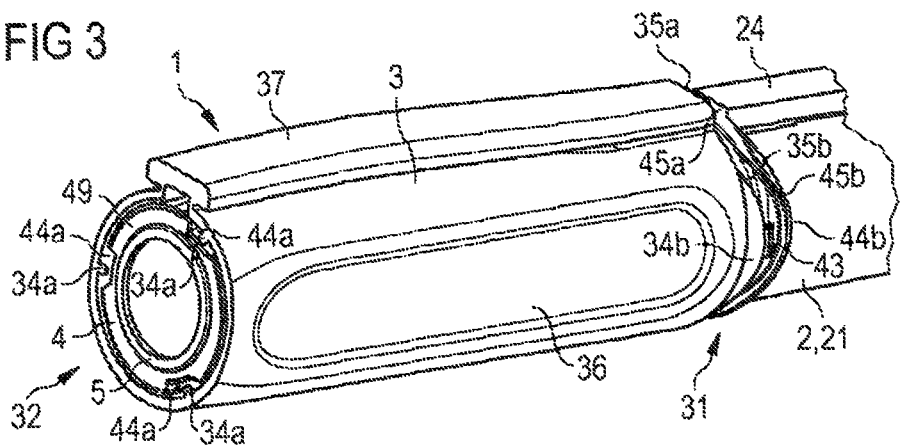
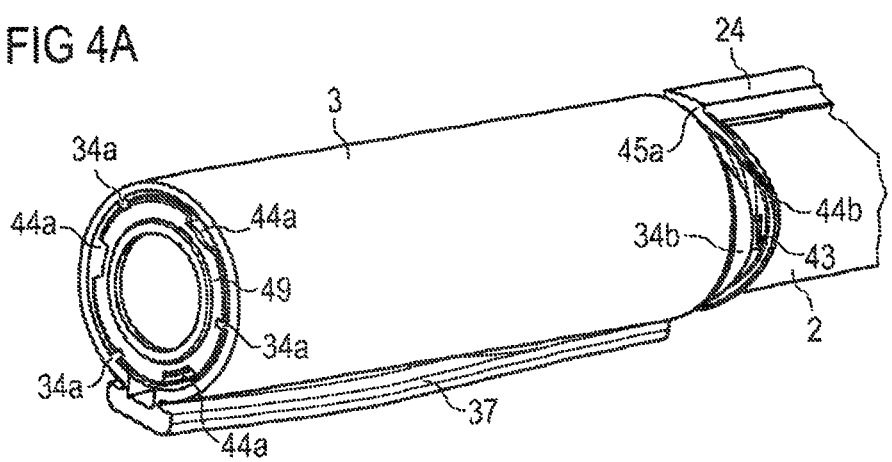
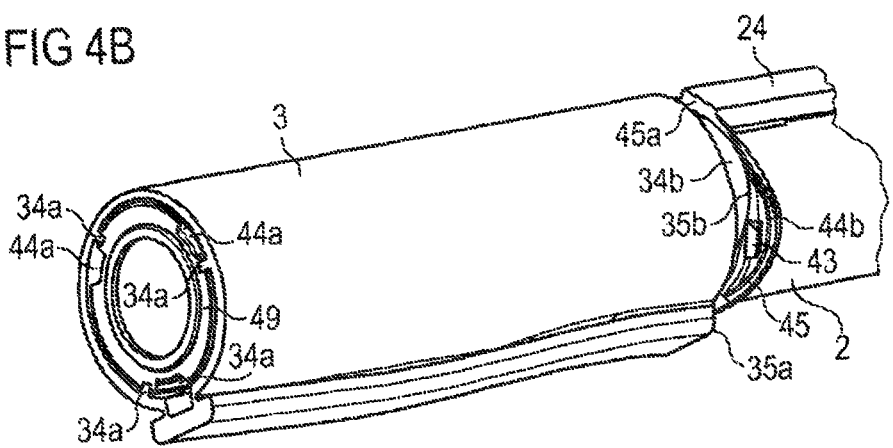

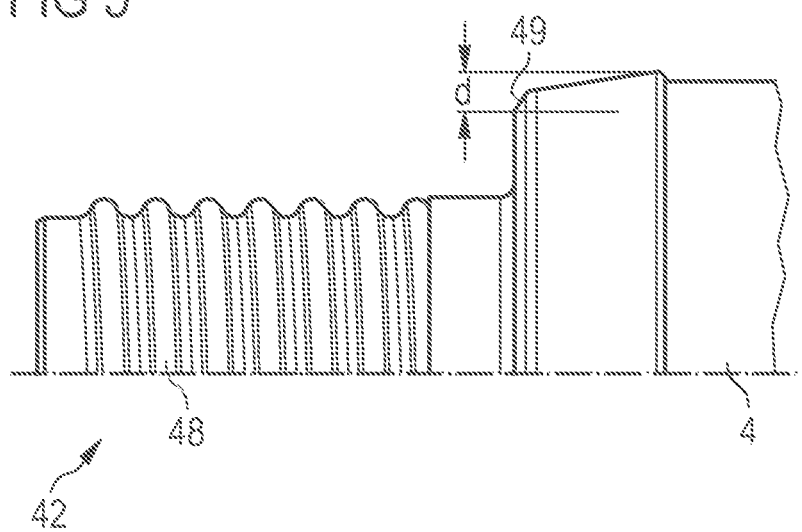

DRUG DELIVERY DEVICE

CROSS REFERENCE TO RELATED APPLICATIONS

The present application is a U.S. National Phase Application pursuant to 35 U.S.C. §371 of International Application No. PCT/EP2009/067477 filed Dec. 18, 2009, which claims priority to EP Patent Application No. 08022318.3 filed on Dec. 23, 2008. The entire disclosure contents of these applications are herewith incorporated by reference into the present application.

FIELD OF THE INVENTION

This disclosure relates to a drug delivery device comprising a cap which can be attached to a housing of the device. In particular, it relates to a cap which can be attached to the housing only in a single orientation relative to the housing.

BACKGROUND

The patent application EP 1923083 A1 discloses an injection device for setting and dispensing a fixed dose of a medicament. Here, a removable cap can be releasably retained over a distal end of a cartridge retaining part.

The patent EP 1007115 B1 discloses an injection device comprising a cap having a curved edge at its open end.

It is an aim of the present invention to provide a drug delivery device, wherein a cap can be attached to a housing in a defined orientation and wherein an attachment in a wrong orientation is efficiently prevented.

SUMMARY

According to a first aspect of the present invention, a drug delivery device is provided comprising a housing and a cap attachable onto the housing. The cap comprises one or more snap features to attach the cap onto the housing and one or more orientation features to define the orientation of the cap relative to the housing when the cap is attached to the housing. At least one of the orientation features is located at a rigid part of the cap and at least one of the snap features is located at a less rigid part of the cap.

The drug delivery device may be a pen-type injection device comprising a cartridge holder configured to receive a cartridge containing a drug. The drug may be medication. Preferably, the cap is attachable onto the device such that it covers at least a part of the cartridge holder. This is useful for protecting the cartridge, in particular when the cartridge is made of a breakable material like glass, or for protecting a needle unit at the distal end of the cartridge holder.

The cap may comprise a window through which information provided by the cartridge or the cartridge holder is visible for the user. As examples, the information may be related to the type or name of the drug contained in the cartridge or may be an indication of the filling status of the cartridge. In the case that the information is visible only when the cap is attached in a certain orientation relative to the housing, the appropriate rotational orientation of the cap has to be ensured.

For this aim, the cap comprises one or more orientation features. In a preferred embodiment, the housing comprises one or more mating orientation features which interact with at least one of the orientation features of the cap. Preferably, for each orientation feature on the cap a mating orientation feature on the housing is provided.

If all orientation features were located at a flexible part of the cap, i.e., a part where the cap can easily be elastically deformed, the cap might be attachable to the housing also in a wrong orientation. Here, the cap may be forced onto the housing by a deformation at its flexible part where the orientation features are located and thereby, the orientation features bump over the mating orientation features of the housing. However, for an orientation feature which is located at a rigid part of the cap, such an elastic deformation and the resulting "bump over" may be prevented.

At least one of the snap features of the cap is located at a less rigid part of the cap. In a preferred embodiment, the housing comprises at least one mating snap feature which is engageable with at least one of the snap features of the cap. For the engagement of a snap feature with a mating snap feature, a certain elastic deformability of the cap may be required. Preferably, for every snap feature on the cap a mating snap feature on the housing exists.

Accordingly, the separate positioning of at least one orientation feature at a rigid part of the housing and of at least one snap feature at a less rigid part of the housing allows a reliable attachment of the cap at the right orientation relative to the housing.

The drug delivery device may have a longitudinal axis. In this case, the cap may extend along the longitudinal axis, and the rigidity of the cap may vary along the longitudinal axis. Here, the snap feature located at a less rigid part of the cap and the orientation feature located at a rigid part of the cap may have an offset along the longitudinal axis.

The cap may comprise an open end and a closed end. Preferably, at least one of the snap features is located near the open end of the cap and the orientation feature located at a rigid part of the cap is displaced from the snap feature in a direction towards the closed end of the cap. Preferably, the cap is more rigid at its closed end than at its open end. This means that the cap can be more easily elastically deformed at its open end than at its closed end. As an example, the cap may be of a plastic material such as polypropylene which may be easily deformable at the open end of the cap.

In one embodiment, the orientation feature comprises a rib. The rib may extend towards a longitudinal axis of the drug delivery device. Preferably, the housing comprises a groove where the rib can engage.

The cap may comprise several orientation features, wherein the orientation features in combination ensure that the cap is attached in the right orientation onto the housing. Here, some of the orientation features may be located at a rigid part of the cap and others may be located at a less rigid part of the cap.

In a preferred embodiment, the drug delivery device comprises a plurality of orientation features which have an angular offset around the longitudinal axis.

Preferably, these orientation features simultaneously interact with mating orientation features of the housing or with parts of the housing which prevent an attachment of the cap. By the simultaneous interaction of many orientation features a maximum counterforce can be achieved when a user tries to attach the cap in a wrong orientation.

In a preferred embodiment, several orientation features are located at the same axial position and at an angular offset relative to the longitudinal axis.

In this case, the misplacement of the cap can be prevented efficiently even if a clearance between the inside diameter of the cap and the outside diameter of the housing exists. If only one orientation feature was present at a certain position about the longitudinal axis, there would be a high risk that the cap would be assembled on the housing off axis without the orientation feature preventing the full assembly. However, in the case that several orientation features, e.g. two diametrically opposed orientation features, are provided at certain positions, these may prevent the assembly unless the correct orientation is found.

In a preferred embodiment, several orientation features are located equiangular around the longitudinal axis of the device.

In this case, due to the symmetry, several orientations of the cap relative to the housing may be allowed. In order to allow only one single orientation, some of the orientation features may be located at other positions of the cap. When placing several orientation features at equiangular positions, either all or none of these orientation features interact with mating orientation features. Thereby, a maximum counterforce is exerted when a user tries to assemble the cap in the wrong orientation. In a preferred embodiment, the cap comprises three orientation features which are located at equiangular positions around the longitudinal axis.

In one embodiment, the mating orientation features on the housing comprise a lead-in to assist the assembly of the cap and the housing in the correct orientation.

Thereby, the cap may be guided into the right orientation when a user tries to assemble the cap onto the housing in an orientation slightly deviating from the right orientation. The lead-in may also allow a twisting off of the cap from the housing.

In one embodiment, the cap comprises at least one orientation feature which is located at the open end of the cap in addition to one or more orientation features at the rigid, closed end of the cap.

The sum of the orientation features which are arranged at a rigid part of the cap and the orientation features arranged at the open end of the cap may define a single orientation of the cap on the housing.

As an example, the end face at the open end of the cap comprises at least one protrusion. In a preferred embodiment, the end face of the cap comprises two protrusions which are located at equiangular positions around the longitudinal axis. Here, two possible orientations of the cap are allowed. However, in combination with orientation features at the rigid part of the cap, only a single orientation is possible.

Preferably, at least one orientation feature at the rigid part of the cap is located such that the snap feature at the cap does not fully reach a mating snap feature at the housing before the right orientation has been found.

At least one of the snap features of the cap may be located at the protrusion at the open end of the cap.

The drug delivery device may comprise several snap features. Preferably, the snap features are located at a less rigid part of the cap. Also here, some of the snap features may be located at a more rigid part of the cap.

Other features will become apparent from the following detailed description when considered in conjunction with the accompanying drawings.

BRIEF DESCRIPTION OF THE FIGURES

FIG. 3 shows an assembly of a cap and a housing in the right orientation,
FIG. 4A shows an attempted assembly of a cap and a housing in a first wrong orientation,
FIG. 4B shows an attempted assembly of a cap and a housing in a second wrong orientation,
FIG. 5 shows the front part of a cartridge holder.

DETAILED DESCRIPTION

Figure 1:
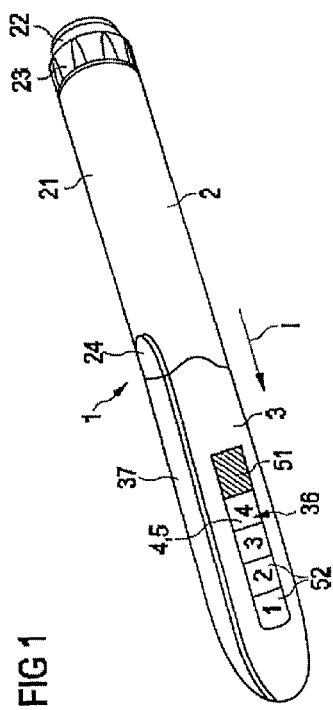
FIG. 1 shows a pen-type injection device comprising a cap.

FIG. 1 shows a pen-type injection device 1 having a longitudinal axis 1.

The injection device 1 comprises a housing 2 with a rear part 21 and a cartridge holder 4, wherein a cartridge 5 is retained. A cap 3 is attached onto the housing 2 and covers the cartridge holder 4.

Through a window 36 in the cap 3, the transparent cartridge holder 4 and the cartridge 5 are visible. A user may set a dose by twisting a dose dial element 23 and inject a dose by pushing a dose button 22. Thereby, a piston 51 in the cartridge 5 is moved forward and the medicament is pressed out of the cartridge 5. The user is informed on the filling status of the cartridge 5 by the position of the piston 51 inside the cartridge 5. A scale 52 at the cartridge holder 5 indicates how many doses are left in the injection device 1. In other embodiments, the scale may be located at the cartridge 5. In order to ensure that the scale 52 is always visible to a user, the cap 3 has to be attached onto the housing 2 in the appropriate orientation.

Figure 2A:
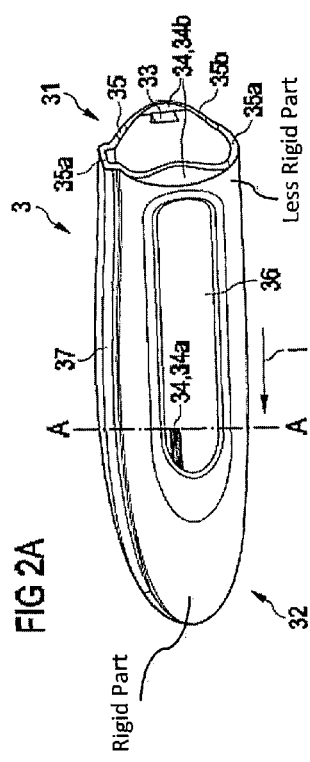
FIG. 2A shows a cap having orientation features and snap features.

FIG. 2A shows a cap 3 having orientation features 34 and snap features 33, whereby the orientation features 34 ensure that the cap 3 can be attached onto the housing 2 only at one specific orientation. The cap 3 comprises a closed end 32 and an open end 31, wherein the closed end 32 is more rigid than the open end 31.

Some of the orientation features 34 are formed as ribs 34a and are located near the closed end 32 of the cap 3. Here, three ribs 34a are arranged at equiangular positions around the longitudinal axis 1.

At its open end 31, the cap 3 comprises orientation features 34 in the form of two protrusions 34b having curved end faces. The protrusions 34b are arranged at diametrically opposed positions.

At the inner surface of each protrusion 34b, a snap feature 33 is located. The end face 35 of the cap 3 also comprises two flat sections 35a arranged between the curved sections 35b of the protrusions 34b.

Figure 2B:
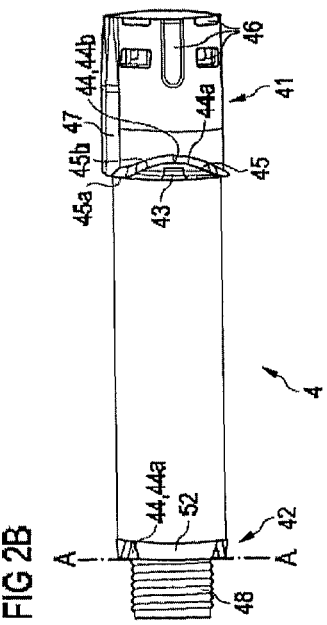
FIG. 2B shows a cartridge holder having mating snap features and mating orientation features.

FIG. 2B shows a cartridge holder 4 which can be attached to the rear part 21 of the housing 2 of an injection device 1. For this aim, the cartridge holder 4 comprises locking means 46 which engage with mating locking means at the rear part 21 of the housing 2 when the rear part 41 of the cartridge holder 4 is inserted into the housing 2.

At its front part 42, the cartridge holder 4 comprises a thread 48, where a needle unit (not shown here) can be attached. The cartridge holder 4 can be covered by the cap 3 as shown in FIG. 1.

For a releasable attachment of the cap 3, the cartridge holder 4 comprises mating snap features 43 which are engagable with the snap features 33 of the cap 3.

Moreover, the cartridge holder 4 comprises mating orientation features 44 which, by interaction with the orientation features 34 of the cap 3, ensure that the cap 3 can be attached onto the housing 2 only at a single orientation.

At a front face 49 near the thread 48, the cartridge holder 4 comprises three grooves 44a where the ribs 34a of the cap 3 can engage. The grooves 44a have a generous lead-in to aid the location of the ribs 34a and to enable the user to twist off the cap 3 in order to remove it. In particular, the grooves 44a are broader than the ribs 34a, such that the ribs 34a may engage also when an orientation near the correct orientation has been found, and have inclined side faces.

Towards the rear part 41 of the cartridge holder 4, two diametrically opposed recesses 44b are formed. By the recesses 44b, mating orientation features 44 for the protrusions 34b of the cap 3 are provided. At the recesses 44b, the cartridge holder 4 has a flank profile 45 which matches the end face 35 of the cap 3. Accordingly, the flank profile 45 comprises a mating flat section 45a and a mating curved section 45b, whereby the twisting off of the cap 3 is enabled.

FIG. 3 shows an assembly of the cap 3 and the housing 2 in the appropriate orientation. Here, the cartridge holder 4 as shown in FIG. 2B has been fixed to the rear part 21 of the housing 2 by its locking means 46 and is covered by the cap 3. Both the cap 3 and the rear part 21 of the housing 2 comprise a rail 37, 24, whereby a user can easily visually identify the correct orientation of the cap 3 on the housing 2. The front part 32 of the cap 3 and the underlying cartridge holder 4 and cartridge 5 is shown in a cross sectional view at the locations marked by the lines A-A in FIGS. 2A and 2B.

In FIG. 3, the ribs 34a of the cap 3 are in the correct orientation to engage with the mating grooves 44a of the cartridge holder 4. Also the protrusions 34b of the cap 3 are in the correct orientation to engage with the recesses 44b of the cartridge holder 4. In this orientation, the cap 3 can be fully assembled onto the housing 2 such that the snap features 33 of the cap 3 can engage with the mating snap features 43 at the cartridge holder 4. By the engagement of the snap features 33 and the mating snap features 43, the cap 3 is attached to the housing 2.

FIG. 4A shows an attempted assembly of a cap 3 and a housing 2 in a first wrong orientation. Here, the cap 3 is out of position by 180°, which can easily be seen by the mismatch of the rail 37 on the cap 3 and the rail 24 on the housing 2. At this orientation, the ribs 34a of the cap 3 cannot engage with the grooves 44a. A further assembly of the cap 3 on the housing 2 is blocked by the abutment of the front end of the ribs 34a and a front face 49 of the cartridge holder 4, although the protrusions 34b would allow an assembly of the cap 3 onto the housing 2. The ribs 34a are located such that an assembly is blocked before the snap features 33 on the cap 3 can engage with the mating snap features 43. Thus, in a wrong orientation, the orientation features 34 prevent both the full assembly and the attachment of the cap 3 onto the housing 2.

FIG. 4B shows an attempted assembly of a cap 3 and a housing 2 in a second wrong orientation. Here, the cap 3 as shown in FIG. 4A has been rotated such that the ribs 34a are about to engage with the grooves 44a. However, at this orientation, the curved end faces of the protrusions 34b abut with the flat sections 45a of the cartridge holder 4, whereby the engagement of the ribs 34a is prevented due to the axial offset caused by the position of the protrusions 34b. The cap 3 can be rotated relative to the housing 2 with the protrusions 34b abutting the flank profile 45 until the correct orientation has been found and the cap 3 can be pushed fully home. In that case, the snap features 33 of the cap 3 engage with the mating snap features 43 of the cartridge holder 4. The cap 3 may be removed by applying a twisting, or a combined twisting and pulling action to the cap 3 relative to the housing 2.

FIG. 5 shows the front part 42 of a cartridge holder 4. Here, at the front face 49 only a limited material thickness d for the grooves 44a is available. Therefore, preferably, at least two or more orientation features 34 on the cap 3 and mating orientation features 44 on the cartridge holder 4 are provided. In this case, also when the cap 3 is assembled off axis, at least one of the orientation features 34 will block the full assembly of the cap until the correct orientation has been found.

Other implementations are within the scope of the following claims. Elements of different implementations may be combined to form implementations not specifically described herein.

The invention claimed is:

1. A drug delivery device comprising:
a housing having a distal end,
a cap having a rigid part and a second part less rigid than the rigid part, where the cap is attachable to the distal end of the housing and configured to cover a cartridge holder attached to the distal end of the housing,
wherein the cap comprises one or more snap features to attach the cap onto the housing and one or more orientation features to define the orientation of the cap relative to the housing when attached to the housing,
wherein at least one of the one or more orientation features is located at the rigid part of the cap and at least one of the one or more snap features is located at the second less rigid part of the cap.

2. The drug delivery device according to claim 1, wherein the one or more orientation features allow a full assembly or attachment of the cap and the housing only in a single orientation of the cap relative to the housing.

3. The drug delivery device according to claim 1 having a longitudinal axis (I),
wherein the at least one snap feature located at the second less rigid part of the cap and the at least one orientation feature located at the rigid part of the cap have an offset according to the longitudinal axis (I).

4. The drug delivery device according to claim 3, comprising a plurality of orientation features having an angular offset around the longitudinal axis (I).

5. The drug delivery device according to claim 1, wherein the cap comprises an open end and a closed end and
wherein at least one of the one or more snap features is located near the open end of the cap and at least one of the one or more orientation features is displaced from this snap feature in a direction towards the closed end of the cap.

6. The drug delivery device according to claim 5, wherein at least one of the one or more orientation features is located at the open end of the cap.

7. The drug delivery device according to claim 6, wherein the cap comprises at least one protrusion at its open end.

8. The drug delivery device according to claim 7, wherein the cap comprises two protrusions at its open end which are located equiangular around the longitudinal axis (I).

9. The drug delivery device according to claim 7, wherein at least one of the one or more snap features is located at the protrusion.

10. The drug delivery device according to claim 1, wherein the housing comprises one or more mating snap features engageable with at least one of the one or more snap features and one or more mating orientation features interacting with at least one of the one or more orientation features.

11. The drug delivery device according to claim 10, wherein the mating orientation features comprise a lead-in to assist the assembly or attachment of the cap and the housing.

12. The drug delivery device according to claim 1, wherein the housing comprises a cartridge holder configured to receive a cartridge containing a drug and wherein the cap can be attached such that it covers at least a part of the cartridge holder.

13. The drug delivery device according to claim 1, wherein the cap comprises a window.

14. The drug delivery device according to claim 13, wherein one of or both a cartridge and a cartridge holder have an indication which is visible through the window when the cap is attached to the housing.

15. The drug delivery device according to claim 1, wherein the drug delivery device is a pen-type injection device.

\* \* \* \* \*